United States Patent [19]

Ghosh et al.

[11] 4,329,428

[45] May 11, 1982

[54] METHANE PRODUCTION FROM AND BENEFICIATION OF ANAEROBIC DIGESTION OF PLANT MATERIAL AND ORGANIC WASTE

[75] Inventors: Sambhunath Ghosh, Homewood; Donald L. Klass, Barrington, both of Ill.

[73] Assignee: United Gas Pipe Line Company, Houston, Tex.

[21] Appl. No.: 117,374

[22] Filed: Jan. 31, 1980

[51] Int. Cl.³ .............................................. C12P 5/02
[52] U.S. Cl. .................................. 435/167; 435/801; 210/603; 210/611
[58] Field of Search ............... 435/167, 801, 822, 253; 210/603, 610, 605, 611, 612; 48/197 FM, 197 A

[56] References Cited

U.S. PATENT DOCUMENTS

| | | | |
|---|---|---|---|
| 1,990,523 | 2/1935 | Buswell et al. | 435/167 |
| 3,640,846 | 2/1972 | Johnson | 435/167 |
| 4,022,665 | 5/1977 | Ghosh et al. | 435/167 |
| 4,040,953 | 8/1977 | Ort | 435/167 X |

OTHER PUBLICATIONS

Nelson et al. "Effect of Temperature of Digestion, Chemical Composition and Size of Particles on Production of Fuel Gas From Farm Wastes", J. Ag. Res. vol. 58 (1939) pp. 273–287.

*Primary Examiner*—R. B. Penland
*Attorney, Agent, or Firm*—Thomas W. Speckman

[57] ABSTRACT

A process for improved methane production resulting in higher yield and higher production rates by anaerobic digestion of a mixture of plant material and organic waste. The process is suitable for production of synthetic natural gas and through anaerobic digestion of a mixture of plant material and organic waste allows better matching of organic waste and plant material feed supplies for year round operation. The process of this invention results in digester effluent which is easily dewatered and has a low concentration of soluble organics, providing easy disposal and recycling to the digester. The process of this invention may be used for methane production from plant material which is, by itself, recalcitrant to anaerobic digestion.

13 Claims, No Drawings

METHANE PRODUCTION FROM AND BENEFICIATION OF ANAEROBIC DIGESTION OF PLANT MATERIAL AND ORGANIC WASTE

BACKGROUND OF THE INVENTION

1. Field of the Invention

Methane production by anaerobic digestion has been widely practiced, particularly with respect to digestion of sewage sludge organic waste. In recent times, the world-wide energy shortage has furthered consideration and improvement of such non-fossil sources of energy. This invention relates to a process for improved methane production from and beneficiation of anaerobic digestion comprising anaerobic digestion of mixtures of plant material and organic waste. The process may be carried out under mesophilic or thermophilic temperatures for detention times in excess of about five days. Particularly preferred is for the plant material to consist of terrestrial and aquatic plant materials. Under steady state anaerobic digestion, the mixed feed blend of plant material and organic waste results in synergistic action providing higher methane yields and production rates than those that result from the anaerobic digestion of the individual feed components separately.

2. Description of the Prior Art

The production of methane gas by anaerobic digestion of various organic wastes has been known. There have been continuous efforts to improve methane yield resulting from anaerobic digestion. Most of the prior attempts to increase methane yield have been centered around anaerobic digestion as practiced in municipal waste treatment plants as exemplified by U.S. Pat. Nos. 3,640,846, teaching addition of coal; 3,981,800, teaching pressurized digestion; and 4,022,665, teaching two phase digestion of sewage sludge. Other attempts to improve the production rate and yield of methane by anaerobic digestion have related to improved anaerobic digestion by utilization of liberated enzymes of the biomass for contribution to more efficient digestion as taught by U.S. Pat. No. 3,994,780. The U.S. Pat. No. 3,994,780 teaches the applicability of its process to a wide variety of organic feeds, but does not suggest the synergistically improved methane production by anaerobic digestion of a mixture of plant material and organic waste. The anaerobic digestion of terrestrial plant material to produce methane has been recognized as exemplified by D. L. Klass and S. Ghosh, "Methane Production by Anaerobic Digestion of Bermuda Grass", presented at symposium on Biomass as a Non-fossil Fuel Source, ACS/Chem. Soc. of Japan Joint Chemical Congress, Honolulu, Hawaii, Apr. 1-6, 1979. Likewise, the anaerobic digestion of aquatic plant material to produce methane has been recognized as exemplified by R. P. Lecuyer and J. H. Marten, "An Economic Assessment of Fuel Gas from Water Hyacinths", Symposium Papers, Clean Fuels from Biomass, Sewage, Urban Refuse, Agricultural Wastes, Orlando, Fla., Jan. 27-30, 1976. Again, the synergism resulting in improved methane production by anaerobic digestion of a mixture of plant material and organic waste is not suggested. Stimulation of methane production in anaerobic waste treatment by metal cations has been recognized as has the problem of toxicity in methane producing anaerobic systems as exemplified by I. J. Kugelman and K. K. Chin, "Toxicity, Synergism and Antagonism in Anaerobic Waste Treatment Processes", Anaerobic Biological Treatment Processes, Advances in Chemistry, Series 105 (1971). While recognizing the sensitivity of methane production in anaerobic waste treatment processes, there is no suggestion of the synergism of anaerobic digestion of a mixture of plant material and organic waste in methane production.

SUMMARY OF THE INVENTION

The process of this invention provides production of methane gas in higher yields and higher rates by thermophilic or mesophilic anaerobic digestion of a mixture of plant material and organic waste. The resulting methane yields and production rates are higher than those obtained by the sum from anaerobic digestion of the individual feed components. The plant material may be of terrestrial or aquatic origin. It is particularly preferred that the plant material be a mixture of terrestrial and aquatic plant materials.

The term "plant material" as used in this description and the appended claims includes any of the organisms of the kingdom of Plantae which typically have cell walls composed of cellulose in large part and have nutritive systems in which carbohydrates are formed photosynthetically. The plant material useful in this invention is fresh harvested or stored plant material, which is usually grown on farms for this purpose, and is untreated chemically or physically, except for size reduction. Included are both terrestrial plants and aquatic plants. Terrestrial plants include warm season grasses, such as Bermuda grass and Elephant grass; cool season grasses, such as Kentucky Blue grass and Merion Blue grass; reedy plants, such as Bamboo, rice, cattails; herbaceous plants, such as Kudzu and maze; deciduous trees, such as eucalyptus and poplar; and coniferous trees, such as white and red pines. Exemplary aquatic plants include water hyacinth, duck weed, algae, sea kelp and sargassum.

By the term "organic waste" as used in this disclosure and the appended claims, we mean all types of organic refuse including sewage sludge, animal waste, municipal waste, industrial waste, forestry waste, agricultural waste, and the like. By forestry waste and agricultural waste we mean to include portions of plants after some physical or chemical treatment, usually not including the entire plant, for example, stumps from logging, sawdust, wood chips, corn stalks, corncob and bagasse. Treatment of municipal solid waste and industrial solid waste for removal of undesired material such as glass, metals, plastics, stones, and the like, is well known to the art.

It is suitable for the feed mixture to comprise more than an inoculant amount of each plant material and organic waste. The plant material and organic waste are the principal feed materials, suitably in proportions of about 10 to about 90 weight percent on a dry solids basis of plant material and about 10 to about 90 weight percent on a dry solids basis of organic waste. Particularly preferred are mixtures comprising about 30 to about 70 weight percent on a dry solids basis of each portion of plant material and organic waste. Mixtures of individual organic wastes as defined above may be used. Particularly preferred are mixtures of municipal waste, industrial waste and sewage sludge. Mixtures of individual plant materials as defined above may be used. Particularly preferred are mixtures of terrestrial and aquatic plant materials. When a mixture of terrestrial plant material and aquatic plant material is used, it is suitable for the feed mixture to consist of about 10 to 80 weight percent on a dry solids basis of each of the components, organic waste, terrestrial plant material and aquatic plant material, about 20 to about 60 weight percent on a dry solids basis of each of the components being preferred. Known techniques may be used for simultaneous digestion of the plant material and organic waste. Detention times of in excess of 5 days and preferably about 8 to about 30 days are suitable. Detention times of about 11 to about 16 days are especially preferred. Increases of methane yield of greater than about 25 percent and up to over 100 percent are obtained by blending of plant material and organic waste for anaerobic digestion feed. Methane production by anaerobic digestion according to the process of this invention using anaerobic digestion of a mixture of plant material and organic waste can be continued for long periods of time without addition of external nutrient. Methane production is stable over long periods of digestion. Plant materials, for example herbacious plants such as Giant Reed, bamboo and grasses and woody plants such as Black Alder, Loblolly Pine, Eucalyptus and Box Elder which are recalcitrant to anaerobic digestion alone are readily digested using the process of this invention involving mixed plant material-organic waste feed. The effluent from the anaerobic digestion of a mixture of plant material and organic waste has a low concentration of soluble organics indicating low ultimate disposal cost and the feasibility of its recycle to the anaerobic digester with little or no treatment. The digested effluent, although dilute, can be dewatered directly by vacuum filtration to provide cake-solids content and cake yield comparable to that of filtered, digested sewage sludge.

It is an object of this invention to provide a process for methane production resulting in higher yields and higher production rates than previously obtained by the separate anaerobic digestion of organic wastes and plant materials.

It is another object of this invention to provide a process for methane production by anaerobic digestion of a mixture of plant material and organic waste which does not require addition of external nutrient throughout the process.

It is yet another object of this invention to provide a process for methane production by anaerobic digestion resulting in digester effluent which can be easily dewatered.

It is still another object of this invention to provide a process for methane production of anaerobic digestion resulting in the digester effluent having low concentration of soluble organics providing easy disposal and recycling to the digester with little or no treatment.

It is another object of this invention to provide a process for methane production from plant material which is, by itself, recalcitrant to anaerobic digestion.

It is another object of this invention to provide a process suitable for production of synthetic natural gas (SNG) by an anaerobic digestion process comprising anaerobic digestion of a mixture of plant material and organic waste, thereby allowing better matching of organic waste and plant material feed supplies for continuous year round operation.

Yet another object of this invention is to provide a hybrid plant material-organic waste methane production plant providing simultaneous energy recovery and waste stabilization.

These and other objects and advantages are achieved by the process of this invention as set forth in the more detailed description of preferred embodiments.

DESCRIPTION OF THE PREFERRED EMBODIMENTS

The anaerobic digestion of plant material and organic waste according to this invention comprising anaerobic digestion of a mixture of plant material and organic waste and removal of methane containing gas from the digestion zone may be carried out under conditions of temperature, both mesophilic (about 20° to 45° C.) and thermophilic (about 45° to 70° C.); detention times in excess of about 5 days and usually about 8 to 30 days, preferably about 11 to 16 days; loading rates; pretreatment of feed; digester mixing and recycling as known to the art for anaerobic digestion and pointed out more particularly in the references identified above. The present invention may be readily applied to multistage digestion, such as exemplified by our earlier U.S. Pat. No. 4,022,665.

An important aspect of the present invention is the anaerobic digestion of a mixture of plant material and organic waste. The plant material and organic waste may be premixed prior to introduction into the digester or the individual feed materials may be separately introduced into the digester and mixed within the digester. The important aspect is that the mixture of plant material and organic waste be together in the active digestion zone. Feeding and associated wasting may be continuous or intermittent.

Any active methane producing mesophilic or thermophilic anaerobic digestion system may be used. Methane-producing anaerobic systems utilizing acid forming bacteria and methane-producing organisms as well known to be employed to produce methane from sewage sludge can be employed in practice of the present invention. A review of the microbiology of anaerobic digestion is set forth in Anaerobic Digestion, 1. The Microbiology of Anaerobic Digestion, D. F. Toerien and W. H. J. Hattingh, Water Research, Vol. 3, pages 385-416, Pergamon Press (1969). As set forth in that review, the principal suitable non-methanogenic bacteria include species from genera including Aerobacter, Aeromonas, Alcaligenes, Bacillus, Bacteroides, Clostridium, Escherichia, Klebsiella, Leptospira, Micrococcus, Neisseria, Paracolobactrum, Proteus, Pseudomonas, Rhodopseudomonas, Sarcina, Serratia, Streptococcus and Streptomyces. Exemplary methane-producing organisms suitable for use in the present invention include members of Methanobacterium, Methanococcus and Methanosarcina, specific members being *Methanobacterium formicicum, Methanosarcina barkerii, Methanobacterium omelianskii, Methanococcus vannielii, Methanobacterium sohngenii, Methanosarcina methanica, Methanococcus mazei, Methanobacterium suboxydans* and *Methanobacterium propionicum*. It is usually preferred to use mixed cultures to obtain the most complete fermentation action. Nutritional balance and pH adjustments may be made to the digester system as is known to the art to optimize methane production from the culture used.

Utilization of a mixture of plant material and organic waste as a feed for the improve methane producing process of this invention overcomes prior problems of seasonable variability of materials for feed stock, such as plant material alone. Further, storage of plant material feed stocks has not been satisfactory and is expensive. The use of a mixture of plant materials according to this invention helps to accommodate the seasonal variability of various species and geographic locations of farms for their production. Utilization of the mixed feed stock of this invention including organic waste provides simultaneous energy recovery in the form of methane and waste stabilization in an integrated process. The methane containing gas produced may be treated by methods known to the art to provide substitute natural gas (SNG).

The process of this invention provides a synergistic yield of methane comprising the steps of digesting in an active mesophilic or thermophilic anaerobic digestion system a mixture of plant material and organic waste, each present in greater than an inoculant amount and withdrawing methane-containing gas from the digestion system. By methane-containing gas we mean the mixture of principally methane and carbon dioxide as produced by anaerobic digestion systems. Various means for increasing methane yield, gas quality and digestion kinetics involving feed pretreatment, residue post-treatment and recycling or advanced digestion modes may be used in conjunction with the process of this invention.

The following specific examples are set forth for the purpose of illustration and should not limit this invention in any way.

EXAMPLE I

Digester feed for anaerobic digestion was prepared by reducing water hyacinth and grass to fine particles by fine extrusion cutting to liberate the cellulose fraction of the fibers from the lignin coating; municipal solid waste was air separated and reduced to fine organic-rich particles by two-stage hammermilling; activated sewage sludge was concentrated by vacuum filtration resulting in solids contents of 62.5 weight percent volatile solids of total solids; and primary sludge was concentrated by centrifugation to 68.2 weight percent volatile solids of total solids. The treated municipal solids waste comprised about 87.4 percent paper and paper products; 4.4 percent plastics; 1.3 percent green garbage; and 6.9 percent miscellaneous including food waste and paper pieces difficult to identify, all on a weight percent basis. The sludge had an elemental analysis as follows:

| | Sludge - Wt. % Dry | |
|---|---|---|
| Elements | Primary | Activated |
| Carbon | 40.10 | 33.40 |
| Nitrogen | 5.04 | 5.31 |
| Phosphorus | 0.83 | 1.10 |
| Sulfur | 0.99 | 0.86 |
| Hydrogen | 5.72 | 4.88 |
| Calcium | 2.00 | 1.70 |
| Sodium | 0.20 | 0.08 |
| Potassium | 0.23 | 0.28 |
| Magnesium | 0.58 | 0.72 | and the major organics in the sludge were:

| | Sludge - Wt. % Dry Solids | |
|---|---|---|
| Material | Primary | Activated |
| Cellulose | 11.5 | 9.5 |
| Hemicellulose | 23.2 | 18.1 |
| Lignin | 1.8 | 1.4 |
| Crude Protein | 31.5 | 33.2 |
| Ash | 32.1 | 37.9 |

Digester start up was achieved with a mixed inoculum, 70 volume percent derived from an existing mesophilic anaerobic digester fed with sea kelp (*Macrocystis pyrifera*) and operated at a loading of 0.1 lb. VS/ft$^3$-day for detention time of 18 days and 30 volume percent derived from another existing mesophilic anaerobic digester fed with mixed primary-activated sewage sludge operated at a loading of 0.8 lb. VS/ft$^3$-day for detention time of 5.6 days. The mixed inoculum contained a diversity of acid forming and methane producing microorganisms as set forth in the Toerien and Hattingh article. (Ibid) The digesters were operated with 70 weight percent sea kelp and 30 weight percent sludge on a VS basis with daily feeding and wasting to increase culture volumes by 10% per day to the desired culture volume of about twice the initial inoculum volume. Loading was maintained at 0.1 lb. VS/ft$^3$-day and detention time of 15 days. The digester then was passed through a feed transition period during which it was fed decreasing amounts of kelp-sludge mixture and increasing amounts of mixed feed materials prepared in the above manner were blended in the following proportions and added to the anaerobic digester:

| Blend 1 | |
|---|---|
| Material | Weight Percent Volatile Solids Basis |
| Water hyacinth | 32 |
| Bermuda grass | 33 |
| Municipal solid waste | 32 |
| Activated sewage sludge | 2 |
| Primary sludge | 1 |

The blend was digested in a semicontinuous completely mixed anaerobic digester at a detention time of 12 days, a loading of 0.1 lb. VS/ft$^3$-day, and a temperature of 35° C. at a pH of 6.8–7.1. The run was continued for six detention times (72 days) and exhibited stable performance. At steady state, methane yields of 3.5 to 4 SCF/lb. VS added were obtained with the gas quality being 62–64 mole percent methane. When each of the feed components was digested separately under the same conditions (detention time, temperature, pH, etc.) of digestion, the sum of the methane yields for a total loading of 0.1 lb. VS/ft$^3$-day was 2.3 to 2.6 SCF/lb. VS added. Thus, an increase in methane yield of about 53% was obtained by blending of organic wastes and plant material for mixed feed for anaerobic digestion. The digester effluent had very low concentration of soluble organics and could be dewatered directly by vacuum filtration providing cake-solids content and cake yield comparable to that of filtered, digested sewage sludge.

EXAMPLE II

Anaerobic digestion was carried out under the same conditions as set forth in Example I with the following blend of feed materials:

| Blend 2 | |
|---|---|
| Material | Weight Percent Volatile Solids Basis |
| Water hyacinth | 40 |
| Bermuda grass | 25 |
| Municipal solid waste | 25 |
| Activated sewage sludge | 5 |
| Primary sludge | 5 |

At steady state, methane yields of 4.5 SCF/lb. VS added were obtained with the mixed feed and 3 SCF/lb.

VS was the sum of methane yields obtained when the components were digested separately.

EXAMPLE III

Anaerobic digestion was carried out on the feed blends as set forth in both Examples I and II under thermophilic temperatures at 55° C. resulting in steady state methane yields of approximately the same as obtained in Examples I and II.

EXAMPLE IV

Digester feeds prepared in accordance with each Example I and Example II were subjected to mesophilic anaerobic digestion temperatures of 35° C. and thermophilic anaerobic digestion temperatures of 55° C., each for a detention time of 12 days and a loading of 0.2 lb. VS (Volatile Solids)/ft$^3$-day. Methane yields obtained at steady state are shown in Table 1

TABLE 1

| | Methane Yields (SCF(Standard Cubic Feet)/lb. VS added) | | | |
|---|---|---|---|---|
| | Components of Blend 1 | | Components of Blend 2 | |
| Temperature | 35° C. | 55° C. | 35° C. | 55° C. |
| Sum of methane produced by components digested separately | 2 | 2 | 2.1 | 2.1 |
| Mixed components digested together | 3 | 4.5 | 4 | 5 |

EXAMPLE V

Anaerobic digestion was performed as described above for a detention time of five days with components of the feed material blends as described in Examples I and II digested separately and digested together, each at loadings of 0.1 lb.VS/ft$^3$-day as described in Example I and 0.2 lb.VS/ft$^3$-day as described in Example IV, and at each mesophilic temperatures of 35° C. and thermophilic temperatures of 55° C. Methane yields obtained at steady state are shown in Table 2.

TABLE 2

| | Methane Yield SCF/lb.VS added | | | | | | | |
|---|---|---|---|---|---|---|---|---|
| Loading | Blend I | | | | Blend II | | | |
| (lb.VS/ft$^3$-day) | 0.1 | | 0.2 | | 0.1 | | 0.2 | |
| Temperature | 35° C. | 55° C. | 35° C. | 55° C. | 35° C. | 55° C. | 35° C. | 55° C. |
| Sum of methane produced by components digested separately | 0.9 | 1.3 | 0.7 | 1 | 0.9 | 1.4 | 0.7 | 1.1 |
| Mixed components digested together | 2 | 3.5 | 1.8 | 3 | 2.5 | 4 | 2 | 3.5 |

EXAMPLE VI

Digester feed of 49 percent Bermuda grass, 48 percent municipal solid waste, 2 percent activated sewage sludge and 1 percent primary sludge, all on a weight percent volatile solids basis, prepared as described in Example I and subjected to anaerobic digestion under the conditions set forth in Example I produced methane yields of 3.5 to 4 SCF/lb. VS added while the sum of separately digested Bermuda grass and municipal solid waste under the same conditions was 2.5 SCF/lb. VS added.

EXAMPLE VII

Water hyacinth was substituted for Bermuda grass in the digester feed of Example VI and digestion carried out under the same conditions with mixed feed producing methane yields of 4 to 4.5 SCF/lb. VS added while the sum of separately digested water hyacinth and municipal solid waste under the same conditions was 3 SCF/lb. VS added.

While in the foregoing specification this invention has been described in relation to certain preferred embodiments thereof, and many details have been set forth for purpose of illustration, it will be apparent to those skilled in the art that the invention is susceptible to additional embodiments and that certain of the details described herein can be varied considerably without departing from the basic principles of the invention.

We claim:

1. In a process of methane production by anaerobic digestion in the presence of acid-forming bacteria and methane-producing organisms at temperatures about 20° to about 70° C. for detention times about 5 to about 30 days, the improvement of obtaining a synergistic yield of methane by digestion of a mixture of plant material and organic waste resulting in production of greater than about 25 percent higher yield of methane than the sum of methane yields produced by separate digestion of said plant material and organic waste under the same conditions consisting essentially of the steps of:

digesting in an active mesophilic or thermophilic anaerobic digestion system in the presence of acid-forming bacteria and methane-producing organisms of a mixture of about 10 to about 90 weight percent on a dry solids basis of organic waste and about 10 to about 90 weight percent on a dry solids basis of plant material which is untreated chemically or physically except for size reduction; and withdrawing methane-containing gas from said digestion system.

2. The process of claim 1 wherein said organic waste comprises municipal solid waste.

3. The process of claim 1 wherein said mixture comprises about 30 to about 70 weight percent on a dry solids basis of organic waste and about 30 to about 70 weight percent on a dry solids basis of plant material.

4. The process of claim 1 wherein anaerobic digestion is carried out under mesophilic temperatures of about 20° to about 45° C. for detention times of about 8 to about 30 days.

5. The process of claim 1 wherein anaerobic digestion is carried out under thermophilic temperatures of about 45° to about 70° C. for detention times of about 8 to about 30 days.

6. The process of claim 1 wherein said plant material consists of both terrestrial and aquatic plant materials.

7. The process of claim 6 wherein said mixture comprises about 10 to about 80 weight percent on a dry solids basis of organic waste about 10 to about 80 weight percent on a dry solids basis of terrestrial plant material and about 10 to about 80 weight percent on a dry solids basis of aquatic plant material.

8. The process of claim 7 wherein said mixture comprises about 20 to about 60 weight percent on a dry solids basis of organic waste, about 20 to about 60 weight percent on a dry solids basis of terrestrial plant material and about 20 to about 60 weight percent on a dry solids basis of aquatic plant material.

9. The process of claim 6 wherein anaerobic digestion is carried out under mesophilic temperatures of about 20° to about 45° for detention times of about 8 to about 30 days.

10. The process of claim 6 wherein anaerobic digestion is carried out under thermophilic temperatures of about 45° to about 70° C. for detention times of about 8 to about 30 days.

11. The process of claim 1 wherein said organic waste comprises municipal solid waste and said plant material comprises a mixture of terrestrial plant material and aquatic plant material.

12. The process of claim 11 wherein said terrestrial plant material comprises Bermuda grass and said aquatic plant material comprises water hyacinth.

13. The process of claim 1 wherein the yield of methane by digestion of a mixture of said plant material and organic waste is at least 40 percent higher than the sum of methane yields produced by separate digestion of said plant material and organic waste under the same conditions.

* * * * *